(12) United States Patent
Tornes et al.

(10) Patent No.: US 7,083,566 B2
(45) Date of Patent: Aug. 1, 2006

(54) GROOVED BRACHYTHERAPY SOURCES

(75) Inventors: Audun Tornes, Oslo (NO); Morten Eriksen, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 10/275,373

(22) PCT Filed: Apr. 12, 2001

(86) PCT No.: PCT/GB01/01677

§ 371 (c)(1),
(2), (4) Date: Feb. 10, 2003

(87) PCT Pub. No.: WO01/87418

PCT Pub. Date: Nov. 22, 2001

(65) Prior Publication Data

US 2003/0153804 A1    Aug. 14, 2003

(51) Int. Cl.
*A61N 5/00* (2006.01)

(52) U.S. Cl. .................................................. 600/3

(58) Field of Classification Search .............. 600/1–8, 600/439, 427, 407; 604/258, 264, 101.01, 604/101.02, 101.04
See application file for complete search history.

(56) References Cited

U.S. PATENT DOCUMENTS

| | | | |
|---|---|---|---|
| 3,351,049 A | 11/1967 | Lawrence | |
| 4,323,055 A | 4/1982 | Kubiatowicz | |
| 4,401,124 A * | 8/1983 | Guess et al. | 600/458 |
| 4,702,228 A | 10/1987 | Russell, Jr. et al. | |
| 4,784,116 A | 11/1988 | Russell, Jr. et al. | |
| 4,805,628 A | 2/1989 | Fry et al. | |
| 4,869,259 A * | 9/1989 | Elkins | 600/458 |
| 4,977,897 A | 12/1990 | Hurwitz | |
| 5,081,997 A | 1/1992 | Bosley, Jr. et al. | |
| 5,201,314 A | 4/1993 | Bosley, Jr. et al. | |
| 5,404,309 A | 4/1995 | Yamamoto et al. | |
| 5,490,521 A * | 2/1996 | Davis et al. | 600/458 |
| 6,632,176 B1 * | 10/2003 | McIntire et al. | 600/439 |
| 2002/0188195 A1 * | 12/2002 | Mills | 600/431 |

FOREIGN PATENT DOCUMENTS

| | | |
|---|---|---|
| EP | 0 668 088 | 8/1995 |
| EP | 0 996 130 | 4/2000 |
| WO | 98/27888 | 7/1998 |
| WO | WO 00/28554 | 5/2000 |

OTHER PUBLICATIONS

J.C. Blasko, et.al. The Urological Clinics of North America, 23, 663-650 (1996).
H. Ragde, et.al., Cancer, 80, 442-453 (1997).
R Waksman, Vascular Radiotherapy Monitor, 1998, 1. 10-18.
MedPro Month, Jan. 1998, pp. 26-32.
Grimm, P.D., et.al., Atlas of the Urological Clinics of North America, vol. 2., No. 2, 113-125 (1994).
McGahan, J.P., in " Laboratory assessment of ultrasonic needle and cathether visualisation." Journal of Ultrasound In Medicine, 5(7), 373-7 (Jul. 1986).

* cited by examiner

*Primary Examiner*—Samuel G. Gilbert
(74) *Attorney, Agent, or Firm*—Robert F. Chisholm

(57) ABSTRACT

Radioactive sources, preferably radioactive seeds, for use in brachytherapy comprising a radioisotope within a sealed biocompatible container, wherein at least one part of the outer surface of the container is grooved, preferably with a curved groove. The grooved outer surface is preferably substantially free from angularities. Such grooves enhance the echogenicity of the source using medical ultrasound at a greater range of angles to the ultrasound probe, thus enhancing the ultrasound visibility of the source. Preferred radioisotopes are palladium-103 and iodine-125.

13 Claims, 10 Drawing Sheets

Fig.5.
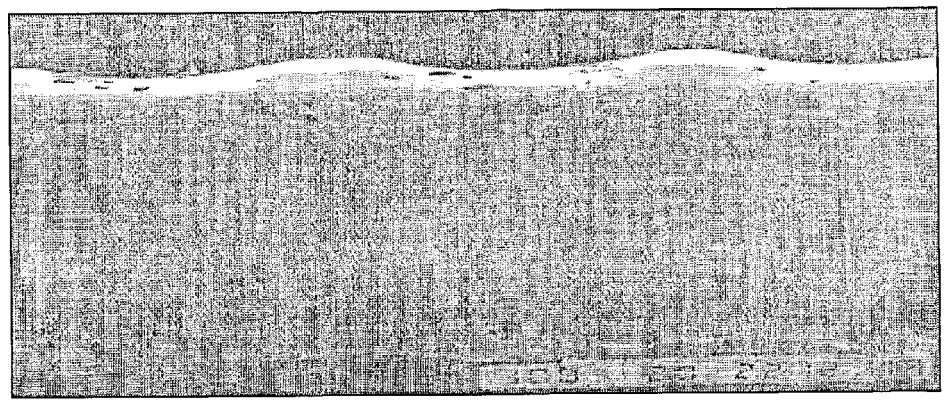
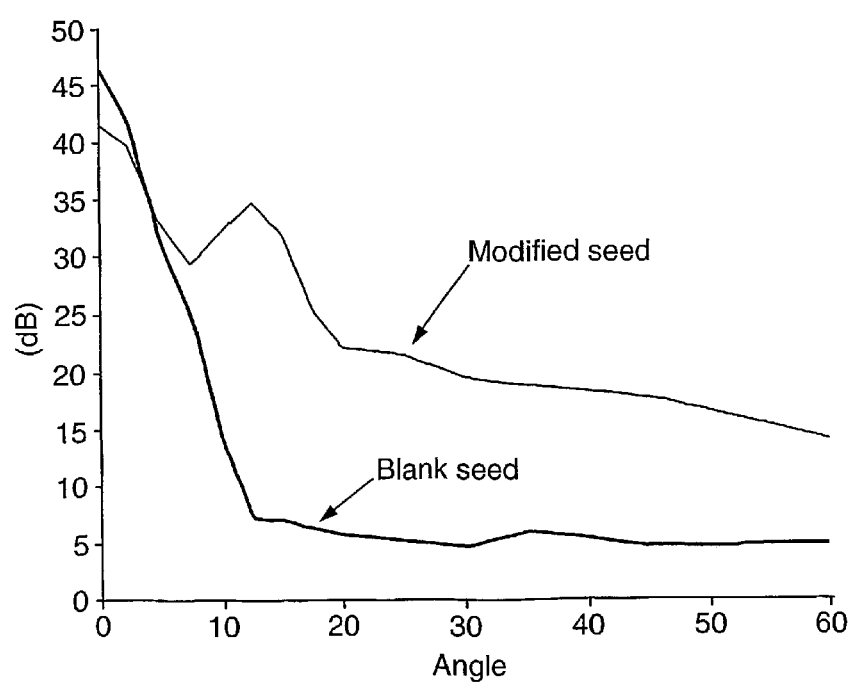

Fig.6.
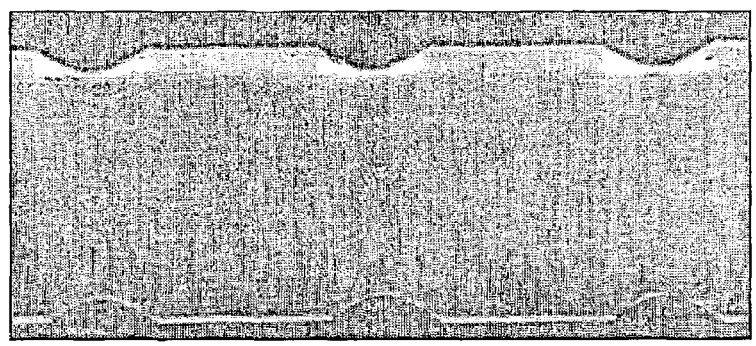
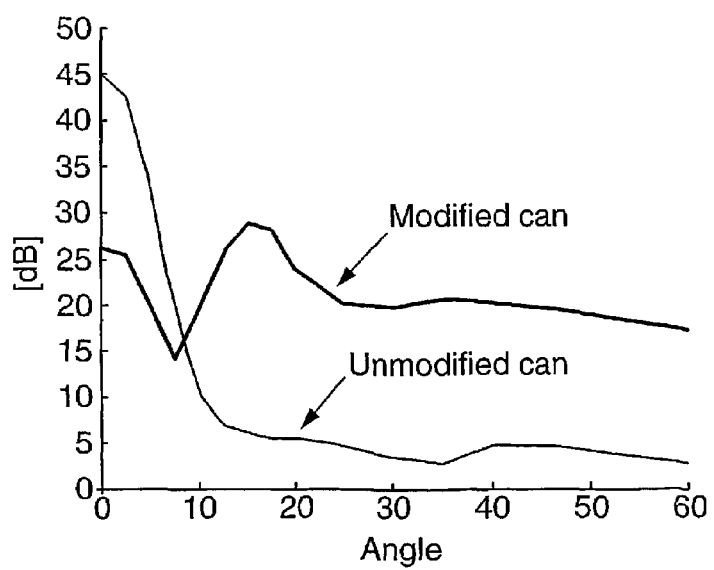

Fig.7B.
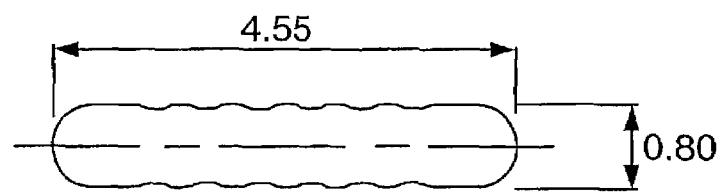
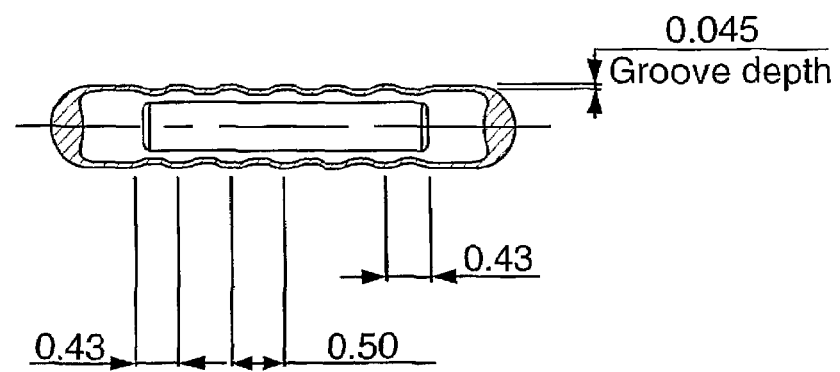

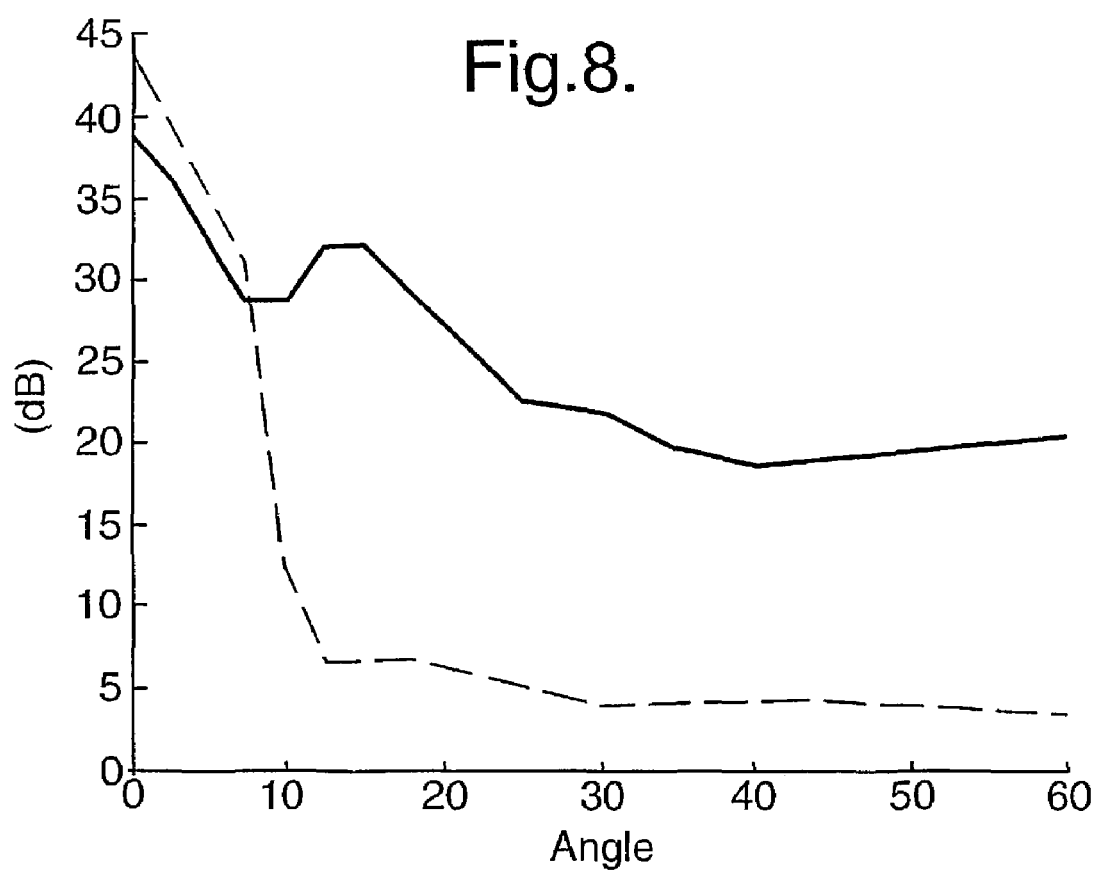

GROOVED BRACHYTHERAPY SOURCES

FIELD OF INVENTION

This invention relates to radiotherapy. More particularly, it relates to radioactive sources for use in brachytherapy, and in particular to grooved radioactive sources, with improved ultrasound imaging visibility.

BACKGROUND OF INVENTION

Brachytherapy is a general term, covering medical treatment which involves placement of a radioactive source near a diseased tissue, and may involve the temporary or permanent implantation or insertion of a radioactive source into the body of a patient. The radioactive source is thereby located in proximity to the area of the body to be treated. This has the advantage that a high dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer, and especially prostate cancer in men (see for example J. C. Blasko et al., The Urological Clinics of North America, 23, 633–650 (1996), and H. Ragde et al., Cancer, 80, 442–453 (1997)). Prostate cancer is the most common form of malignancy in men in the USA, with more than 44,000 deaths in 1995 alone. Treatment may involve the temporary implantation of a radioactive source for a calculated period, followed by its subsequent removal. Alternatively, the radioactive source may be permanently implanted in the patient and left to decay to an inert state over a predictable time. The use of temporary or permanent implantation depends on the isotope selected and the duration and intensity of treatment required.

Permanent implants for prostate treatment comprise radioisotopes with relatively short half-lives and lower energies relative to temporary sources. Examples of permanently implantable sources include iodine-125 or palladium-103 as the radioisotope. The radioisotope is generally encapsulated in a titanium casing to form a "seed" which is then implanted. Temporary implants for the treatment of prostate cancer may involve iridium-192 as the radioisotope.

Recently brachytherapy, in particular intraluminal radiation therapy has been proposed for the treatment of restenosis (for reviews see R. Waksman, Vascular Radiotherapy Monitor, 1998, 1, 10–18, and MedPro Month, January 1998, pages 26–32). Restenosis is a re-narrowing of the blood vessels after initial treatment of coronary artery disease. Various isotopes including iridium-192, strontium-90, yttrium-90, phosphorous-32, rhenium-186 and rhenium-188 have been proposed for use in treating restenosis.

Conventional radioactive sources for use in brachytherapy include so-called seeds. Seeds are smooth sealed sources, which comprise containers or capsules of a biocompatible material (e.g. metals such as titanium or stainless steel), containing a radioisotope within a sealed chamber. The container or capsule material permits radiation to exit through the container/chamber walls (U.S. Pat. Nos. 4,323, 055 and 3,351,049). Such seeds are only suitable for use with radioisotopes which emit radiation which can penetrate the chamber/container walls. Therefore, such seeds are generally used with radioisotopes which emit γ-radiation or low-energy X-rays, rather than with β-emitting radioisotopes.

In brachytherapy, it is vital to the therapeutic outcome for the medical personnel administering the treatment to know the relative position of the radioactive source in relation to the tissue to be treated, i.e. to ensure that the radiation is delivered to the correct tissue and that no localised over or under dosing occurs. Current seeds therefore typically incorporate a marker for X-ray imaging such as a radio-opaque metal (e.g. silver, gold or lead). The location of the implanted seed is then established via X-ray imaging, which exposes the patient to an additional radiation dose. Such radio-opaque markers are typically shaped so that imaging gives information on the orientation as well as location of the seed in the body, since both are necessary for accurate radiation dosimetry calculations.

Permanent implantation of brachytherapy radioactive sources for the treatment of, for example, prostate cancer may be done using an open laparotomy technique with direct visual observation of the radioactive sources and the tissue. However, the procedure is relatively invasive and often leads to undesirable side effects in the patient. An improved procedure comprising transperineal insertion of radioactive sources into predetermined regions of the diseased prostate gland (using an external template to establish a reference point for implantation) has been proposed. See for example Grimm, P. D., et al., Atlas of the Urological Clinics of North America, Vol. 2, No. 2, 113–125 (1994). Commonly, these radioactive sources, for example seeds, are inserted by means of a needle device while an external depth gauge is employed with the patient in the dorsal lithotomy position. For prostate cancer treatment, typically 50 to 120 seeds are administered per patient in a 3-dimensional array derived from multiple needle insertions of linear, spaced seeds. The dose calculation is based on this complex 3-D array, plus data on the tumour volume plus prostate volume etc.

Preferably, the insertion or implantation of a radioactive source for brachytherapy is carried out using minimally-invasive techniques such as, for example, techniques involving needles and/or catheters. It is possible to calculate a location for each radioactive source, which will give the desired radiation dose profile. This can be done using a knowledge of the radioisotope content of each source, together with the dimensions of the source, accurate dimensions of the tissue or tissues in relation to which the source is to be placed, plus the position of said tissue relative to a reference point. The dimensions of tissues and organs within the body for use in such dosage calculations may be obtained prior to placement of the radioactive source by using conventional diagnostic imaging techniques including X-ray imaging, magnetic resonance imaging (MRI) and ultrasound imaging. However, difficulties may arise during the radioactive source placement procedure which may adversely affect the accuracy of the placement of the source if only pre-placement images are used to guide the source placement. For example, tissue volume may change as a result of swelling or draining of fluid to and from the tissue. Tissue position and orientation can change in the patient's body relative to a selected internal or external reference point as a result of for example manipulation during surgical procedures, movement of the patient or changes in the volume of adjacent tissue. Thus, it is difficult to achieve accurate placement of sources to achieve a desired dosage profile in brachytherapy using only knowledge of tissue anatomy and position that was obtained prior to the placement procedure. Therefore, it is advantageous if real-time visualisation of both the tissue and the radioactive source can be provided. A particularly preferred imaging method due to its safety, ease of use and low cost, is ultrasound imaging.

During the placement of the radioactive sources into position, the surgeon can monitor the position of tissues such as the prostate gland using, for example, transrectal ultrasound pulse-echo imaging techniques which offer the advantage of low risk and convenience to both patient and surgeon. The surgeon can also monitor the position of the relatively large needle used in implantation procedures using ultrasound. During the implantation or insertion procedure, the location of the source may be inferred to be proximal to the tip of the needle or other device used for the procedure. However, the relative location of each separate radioactive source should be evaluated subsequent to the implantation procedure to determine if it is in a desired or undesired location and to assess the uniformity of the therapeutic dose of radiation to the tissue. Radioactive sources may migrate within the tissue following implantation.

Ultrasound reflections may be either specular (mirror-like) or scattered (diffuse). Biological tissue typically reflects ultrasound in a scattered manner, whilst metallic devices tend to be effective reflectors of ultrasound. Relatively large smooth surfaces such as those of needles used in medical procedures reflect sound waves in a specular manner. The ultrasound visibility of conventional radioactive seeds is highly dependent upon the angular orientation of the seed axis with respect to the ultrasound transducer used for imaging. The ultrasound reflection from a surface is dependent on the surface shape and can be deduced from diffraction considerations. Thus, a smooth flat surface will generally act as a mirror, reflecting ultrasound waves in the wrong direction unless the angle between the sound and the surface is 90°. A smooth cylindrical structure such as a conventional radioactive seed will reflect waves in a fan shaped conical pattern pointing away from the transducer, but will only give strong ultrasound reflections when imaged at an angle very close to 90°.

Thus, brachytherapy seeds with a smooth titanium surface are effective ultrasound reflectors, but the reflected ultrasound intensity is strongly dependent on the orientation of the seed with respect to the ultrasound beam. Theory and practical experiments show that even at an angle of 8 degrees between the long axis of the seed and the ultrasound transducer (a deviation of 8° from orthogonal), the signal intensity drops by a factor of 100 (20 dB), and the seed becomes difficult to detect. At an orientation of 10 degrees the seed is not possible to detect against a tissue background. Consequently, even very small deviations from orthogonal incidence of the ultrasound beam cause substantial reductions in the intensity of the echo signal. Analysis of clinical X-ray images of the prostate acquired post seed implantation show a wide distribution of seed angular orientations and only a fraction of the seeds are oriented within ±10 degrees.

Thus, the relatively small size of current brachytherapy radioactive sources and the specular reflection properties of their surfaces makes them very difficult to detect by ultrasound imaging techniques.

There is therefore a need for radioactive sources for use in brachytherapy with improved ultrasound imaging visibility, and in particular for sources where the dependence of visibility on the angular orientation of the axis of the source with respect to the ultrasound transducer is reduced. Since the total returned echo intensity is limited by the physical size of the seed, improvements require broadening the angular range of echo return. The present invention provides radioactive sources with improved ultrasound visibility, by reducing the angular dependence of the reflected ultrasound.

Efforts have been made to enhance the ultrasound visibility of surgical apparatus which is relatively larger than seeds, (e.g. surgical needles, solid stylets and cannulae) by suitable treatment of their surfaces such as roughening, scoring or etching. Thus, U.S. Pat. No. 4,401,124 discloses a surgical instrument (a hollow needle device) that has a diffraction grating inscribed on the surface to enhance the reflection coefficient of the surface. Sound waves that strike the grooves are diffracted or scattered as secondary wave fronts in many directions, and a percentage of these secondary waves are detected by the ultrasound transducer. The diffraction grating is provided for use at the leading edge of a surgical instrument for insertion within a body, or for use along a surface of an object the position of which is to be monitored while in the body.

U.S. Pat. No. 4,869,259 discloses a medical needle device that has a portion of its surface particle-blasted to produce a uniformly roughened surface that scatters incident ultrasound, such that a portion of the scattered waves is detected by an ultrasound transducer.

U.S. Pat. No. 5,081,997 discloses surgical instruments with sound reflective particles imbedded in a portion of the surface. The particles scatter incident sound, and a portion is detected by an ultrasound transducer.

U.S. Pat. No. 4,977,897 discloses a tubular cannula device comprising a needle and an inner stylet in which one or more holes are cross-drilled perpendicular to the axis of the needle to improve ultrasound visibility. The solid inner stylet may be roughened or scored to enhance the sonographic visibility of the needle/stylet combination.

WO 98/27888 describes a echogenically enhanced medical device in which a print pattern mask of non-conductive epoxy-containing ink is transfer-coated to the surface of the device, flash dried, and then thermally crosslinked. Portions of the needle not protected by the mask are removed by etching in an electropolishing step to leave a pattern of substantially square depressions in the bare metal, and the ink masked is removed with a solvent and mechanical scrubbing. The depressions provide the device with enhanced echogenicity under ultrasound.

U.S. Pat. No. 4,805,628 discloses a device which is inserted or implanted for long-term residence in the body, which device is made more visible to ultrasound by providing a space in the device which has a substantially gas impermeable wall, such space being filled with a gas or mixture of gases. The invention is directed to IUD's (intrauterine devices), prosthetic devices, pacemakers, and the like.

McGahan, J. P., in "Laboratory assessment of ultrasonic needle and catheter visualisation." Journal of Ultrasound In Medicine, 5(7), 373–7, (July 1986) evaluated seven different catheter materials for their sonographic visualisation in vitro. While five of the seven catheter materials had good to excellent sonographic detection, nylon and polyethylene catheters were poorly visualised. Additionally, various methods of improved needle visualisation were tested. Sonographic needle visualisation was aided by a variety of methods including either roughening or scoring the outer needle or inner stylet and placement of a guide wire through the needle.

WO 00/28554, which is commonly assigned to the present assignee, discloses roughened brachytherapy sources, including seeds, which exhibit enhanced echogenicity. This disclosure shows that the ultrasound visibility of radioactive sources suitable for use in brachytherapy can be improved, even though such sources are relatively much smaller than needles, catheters etc.

Once implanted, seeds are intended to remain permanently at the site of implantation. However, individual seeds may, on rare occasions, migrate within a patient's body away from the initial site of implantation or insertion. This is highly undesirable from a clinical perspective, as it may lead to underdosing of a tumour or other diseased tissue and/or unnecessary exposure of healthy tissue to radiation. There is therefore also a need for radioactive sources for use in brachytherapy which show a reduced tendency to migrate within a patient's body when compared to conventional brachytherapy seeds.

Parameters such as the amplitude and shape of surface irregularities and the distance between repeating surface pattern details determine the angular dependency of echo reflections. As part of the present invention, a large number of prototype samples have been evaluated and a narrow range of seed design options has been identified. A range of surface shapes have been tested: circular and helical sinusoidal and square grooves, triangular grooves, dimples and sandblasted surfaces. Profiles with sharp corners were found to widen the angular range more than smooth shapes. Dimpled surfaces were not found to work as well as grooved surfaces.

SUMMARY OF INVENTION

According to one aspect of the invention, it provides a radioactive source suitable for use in brachytherapy, which comprises a radioisotope within a sealed biocompatible container, where in at least a portion of the outer surface of the container comprises a series of grooves which have:

(i) a depth of 5 to 100 micrometers, (ii) a width of 200 to 500 micrometers, (iii) a spacing of 300 to 700 micrometers.

According to another aspect of the invention, there is provided a method for increasing the ultrasound visibility of a radioactive source for use in brachytherapy with a radioisotope and a sealed biocompatible container, comprising providing the outer surface or part of the outer surface the container with grooves of specific dimensions and arrangement, effective to enhance reflection of ultrasound to thus facilitate detection of the device in vivo.

According to yet another aspect of the invention, there is provided a method for the preparation of a radioactive source comprising a radioisotope and a biocompatible sealed container at least one part of the surface of which is grooved.

According to a further aspect of the invention, there is provided a further method for the preparation of a radioactive source with a radioisotope and a sealed biocompatible container at least one part of the surface of which is grooved, comprising:

(i) grooving a surface or part of the outer surface of a non-radioactive precursor biocompatible container material;

(ii) loading a radioisotope into a suitable sized and sealed grooved biocompatible container precursor from step (i); and (iii) sealing the biocompatible container.

According to a still further aspect of the invention, the invention provides a method of treatment of a condition in a mammal which is responsive to radiation therapy, which comprises the temporary or permanent implantation of a radioactive source comprising a radioisotope within a sealed biomcompatible container, wherein at least one part of the outer surface of the container is provided with the optimised grooves of the present invention, at the site to be treated within a patient for a sufficient period of time to deliver a therapeutically effective dose.

DETAILED DESCRIPTION OF THE INVENTION

According to one aspect of the present invention there is therefore provided a radioactive source suitable for use in brachytherapy, which comprises a radioisotope within a scaled biocompatible container, wherein at least a portion of the outer surface of the container comprises a series of grooves which have:

(i) a depth of 5 to 100 micrometers, (ii) a width of 200 to 500 micrometers, (iii) a spacing of 300 to 700 micrometers.

The grooved surface is optimised to enhance the ultrasound visibility (i.e. the echogenicity) of the source. The design modifications disclosed here involve modifying the outer surface of brachytherapy sources or seeds. Increasing the angular range of ultrasound echo reflection from the source is accompanied by a reduction in the overall echo intensity. Hence, the selected source design will always be a compromise between signal intensity and strength with respect to the angular orientation. Additionally, the source design has to be suitable for reproducible manufacture. The present invention provides an optimised design for echogenic brachytherapy sources for the range of angles of reflection which are of most clinical importance.

The grooved sources of the invention also have the advantage that any tendency for the source to migrate once implanted in a patient's body should be reduced.

Suitable radioisotopes for use in the radioactive brachytherapy sources of the invention are known in the art. Particularly preferred radioisotopes include iodine-125 (I-125) and palladium-103 (Pd-103). A typical titanium seed will contain between 0.15 and 150 millicuries of I-125, so as to emit a dose of between 0.1 and 100 millicuries.

Suitable carriers or substrates for the radioisotope within the biocompatible container may comprise materials such as plastics, graphite, zeolites, ceramics, glasses, metals, polymer matrices, ion-exchange resins or other, preferably porous materials. Alternatively, the substrate may be made of metal, e.g. silver or may comprise a layer of metal plated onto a support material. Suitable support materials include a second metal such as gold, copper or iron, or solid plastics such as polypropylene, polystyrene, polyurethane, polyvinylalcohol, polycarbonate, Teflon™, nylon, delrin and Kevlar™. Suitable plating methods are known in the art and include chemical deposition, sputtering, ion plating techniques, electroless plating and electrodeposition.

The substrate material may be in the form of a bead, wire, filament or rod. Such substrate materials may be encapsulated in a hollow sealed container, for example a biocompatible metal container, to provide a sealed source or "seed", or the carrier may be coated with an electroplated shell, for example a layer of a metal such as silver or nickel. The radioisotope may be physically trapped in or on the substrate, for example by adsorption, or may be chemically attached to it in some way. Alternatively, the source may comprise a hollow sealed container directly encapsulating the radioisotope without the need for a substrate. A suitable method for loading I-125 onto a silver wire substrate is described in U.S. Pat. No. 4,323,055.

Suitable biocompatible container materials include metals or metal alloys such as titanium, gold, platinum and stainless steel; plastics such as polyesters and vinyl polymers, and polymers of polyurethane, polyethylene and poly(vinyl acetate), the plastics being coated with a layer of a biocompatible metal; composites such as composites of graphite, and glass such as matrices comprising silicon oxide. The container may also be plated on the outside with a biocompatible metal, for example titanium, gold or platinum. Titanium and stainless steel are preferred biocompatible metals for such containers, especially titanium.

The radioisotope may also be incorporated into a polymer matrix, or a plastic or ceramic composite, and/or may form part of the container wall. For example, if a metal alloy is used to form a container, then a component of the alloy may be a suitable radioisotope. If a container is made from a composite material, a component of the composite may be a suitable radioisotope.

The radioactive source should be of an overall size and dimensions suitable for its intended use. For example, the overall dimensions are preferably such that the source can be delivered to the treatment site using conventional techniques, for example using a hollow needle or a catheter. Seeds for use in the treatment of prostate cancer are, for example, typically substantially cylindrical in shape and approximately 4.5 mm long (i.e. 4.0 to 5.0 mm long) with a diameter of approximately 0.8 mm (i.e. 0.7 to 1.0 mm diameter), such that they may be delivered to the treatment site using a hypodermic needle. For use in the treatment of restenosis, a source should be of suitable dimensions to be inserted inside a coronary artery, for example a length of about 10 mm (i.e. 2 to 12 mm length), and a diameter of about 1 mm (i.e. 0.5 to 1.5 mm diameter), preferably a length of about 5 mm and a diameter of about 0.8 mm, and most preferably with a length of about 3 mm and a diameter of about 0.6 mm. Sources for use in the treatment of restenosis are typically delivered to the treatment site using conventional catheter and/or guidewire methodology. The grooved sources of the present invention for the treatment of restenosis may also take the form of radioactive stents designed for permanent implantation. Such echogenic stents can be imaged non-invasively using ultrasound both during and after implantation. The sources of the invention may also be substantially spherical in shape. The sources or seeds of the present invention are preferably substantially the same overall physical size as conventional sources. Thus, larger sources will reflect significantly more ultrasound energy, but may introduce handling problems for the clinical user, since in practice the sources or seeds are implanted using needles or cannula of conventional size (e.g. an 18 G needle).

The sources of the invention may be used as permanent implants or for temporary insertion into a patient. The choice of radioisotope and type of source, plus the method of treatment used, depends in part on the condition to be treated.

As used herein, the term "grooved" means a surface or part surface which is not essentially planar as in regular or conventional brachytherapy sources, but which comprises a series of linked raised areas or ridges, and indented areas (or "grooves"), giving an undulating effect. The grooves may be arranged in a regular pattern or may be random, or there may be present a mixture of random and regular regions. Preferably, the grooves are arranged in a regular pattern, and are preferably of curved cross-section. The resulting grooved outer surface is preferably "substantially free from angularities". This term implies that the surface undulations are curved in cross-section, i.e. the undulations form a series of smooth curves, with the minimum of angular or sharp edges. The preferred surface is thus approximately sinusoidal or flattened sinusoidal in profile. Typically, the groove width is 10% to 90%, and preferably 40% to 60% of the groove spacing, in the most preferred aspect wherein the grooves are flattened sinusoidal in profile, the groove width is 50% of the groove spacing. Surface shapes which maximise the variance of the container's outer radius are the most acoustically effective shapes, the flattened sinusoidal surface profile is therefore particularly preferred. The raised areas or ridges may themselves be curved outwards (i.e. be convex), or may be planar. Preferably the raised areas or ridges are planar, and are of uniform disposition so that when, for example, the source is substantially cylindrical in shape, the raised areas form part of the outer surface of the cylinder.

The term "depth" is the amplitude of the groove, i.e. the vertical distance from the bottom of the groove to the top of the groove. For a given groove depth, which may be limited by design and manufacturing constraints, the flattened sinusoidal surface profile provides better distribution of the reflected ultrasound echo than a pattern consisting of narrow depressions.

The grooves of the present invention should not exceed 100 µm in depth or amplitude, since when the amplitude is too large destructive interference may occur, and the reflected intensity at orthogonal incidence is dramatically reduced. Preferred grooves have an amplitude or depth of up to approximately one quarter of a wavelength of the ultrasound involved in water—at an ultrasound frequency of 7.5 MHz, this is about 50 µm (50 micrometers or 0.05 mm). The minimum amplitude of the grooves should be at least 5 µm, preferably about one tenth of a wavelength, i.e. 20 to 30 µm. The suitable range for the amplitude of the grooves is therefore 5 to 100 µm, typically 15 to 75 µm, with 20 to 60 µm being preferred and the range 30 to 50 µm being most preferred. In a particularly preferred aspect, the grooves have a nominal depth or amplitude of 45 µm.

The term "spacing" refers to the distance between the highest points of successive grooves. When the grooves are identical, the spacing is in effect the pattern repetition distance.

By reducing the distance between repeating surface pattern details, the ultrasound reflection at large angles will increase, but the reflection at small angles will be reduced. Hence, for the typical imaging frequencies used the spacing should be 300 to 700 µm (0.3 to 0.7 mm), preferably 400 to 600 µm.(0.4 to 0.6 mm), and most preferably 450 to 550 µm.(0.45 to 0.55 mm). In a particularly preferred aspect, the grooves have a nominal spacing of 500 µm.

The term groove "width" is the distance measured between the two points on the groove which are at a depth equal to the mean outer radius of the biocompatible container. Where the grooves have a symmetrical profile such as sinusoidal, preferably flattened sinusoidal, the groove width will be equal to half of the groove spacing.

The groove width in the sources according to the invention is 200 to 500 micrometers. In a preferred aspect, the grooves have a width of 200 to 300 µm, suitably 225 to 275 µm. In a particularly preferred aspect, where the grooves are flattened sinusoidal in profile and the nominal spacing is 500 µm, the grooves have a nominal width of 250 µm.

The term "series of grooves" means one or more grooves. The grooves should be distributed over a sufficient portion of the outer surface of the container and shaped so that the scattering of ultrasound by the source is adequate for imaging in the range of angles between the ultrasound transducer probe and the seed typical of implanted seeds. This range is anticipated to be able to image the majority of implanted seeds using ultrasound. The grooves may occur over substantially the entire surface of the container, at one or both ends, in the centre or over any other portion of the outer surface. For a radioactive seed, which is substantially cylindrical in shape, typically with top and bottom end welds, the grooves are preferably distributed over the length of the cylinder sides.

The grooves may be arranged randomly on the surface of the source, or in more regular patterns, for example in geometric shapes and patterns such as concentric circles, or as lines running substantially parallel or perpendicular to an axis of the source e.g. in a circumferential arrangement to give bands or corsets, or in a helical arrangement. Helical or parallel groove patterns are preferred, especially in a band or corseted arrangement. Suitable patterns can be readily determined to suit the exact size and shape of the radioactive source concerned. In a preferred aspect of the invention, the container of the radioactive source is provided with 4 to 7, more preferably 6, circumferential circular grooves which are irregularly or regularly, most preferably regularly, spaced along the length of the container.

Preferably, the source will further comprise a radio-opaque substance, for example silver or another metal, such that the sources may be visualised using X-ray imaging techniques in addition to ultrasound imaging. Preferred sources of the invention are sources comprising a metal container or capsule encapsulating a radioisotope, with or without a substrate, and a radio-opaque marker, which can be visualised by both ultrasound and X-ray imaging techniques. Conveniently, the radioisotope may be held on a substrate which is itself radio-opaque, such as a silver wire so as to obviate the need for a separate radio-opaque marker.

One advantage of using the sources of the invention in brachytherapy is that the ultrasound signal and image may be read, measured and analysed by suitable computer software sufficiently quickly to allow a physician to plan real-time dosimetry. This is advantageous from a clinical viewpoint for both patient and medical personnel. However, the sources of the invention may be used in processes involving any type of dosimetry mapping that uses information obtained due to the ultrasound visibility of the sources.

In addition, a physician may use the same imaging technique, i.e. ultrasound, already in place during surgery to confirm both organ (e.g. prostate) position and size, and source placement. This could enable a physician to calculate if additional sources need to be inserted, for example in situations where the dose pattern needs to be recalculated based on the "real" position of the seeds.

The radioactive sources of the invention may be supplied within a substantially linear biodegradable material, for example as in the product RAPID Strand™ available from Medi-Physics, Inc. of Illinois, U.S.A. Preferably the sources are evenly spaced (e.g. 10 mm apart in RAPID Strand™) to permit more even/uniform radiation dosimetry, and the dimensions of the array are such that the whole can be loaded into a needle for administration to a patient. The biodegradable material may be a suture or a suitable biocompatible polymer, and is preferably designed to sufficiently rigid that it can be introduced directly into the human body without deflection. It is anticipated that the strand material will dampen the ultrasound wave from a grooved seed in a strand. A grooved seed in strands is expected to exhibit increased ultrasound visibility (i.e. reflected echo intensity) relative to unmodified seeds in strands. A further aspect of the present invention is therefore grooved brachytherapy sources or seeds in suture or strand type delivery systems.

In a further aspect of the invention, there is provided a method for increasing the ultrasound visibility of a radioactive source for use in brachytherapy comprising a radioisotope and a sealed biocompatible container. The method comprises providing the surface or part of a surface of the container with grooves of specific dimensions and arrangement, effective to enhance reflection of ultrasound to thus facilitate detection of the source in vivo.

In a still further aspect of the invention, there is provided a method for the preparation of a radioactive source comprising a radioisotope and a biocompatible sealed container at least one part of the surface of which is grooved. The grooved surface of the present invention may be produced by a variety of different methods. For example, if the source comprises a radioisotope encapsulated in an essentially cylindrical container or an encapsulating material, then the outer surface of the container or encapsulating material may be grooved by forcing the source through a ridged or serrated die or a threading device to impart grooves on the surface. A similar effect may be produced by milling. Parallel corsets or grooves may be produced by a crimping process using a die tool set. The die set is produced by electrode sparking or etching duplicate sets of grooves into pieces of machined steel, or by high precision milling. The two dies are then polished to a mirror finish so that they meet precisely once pressed together. The titanium tube is inserted into the grooved area of the die set, and the two dies brought together, thus introducing grooves into the surface of the titanium. The depth of the grooves obtained is controlled by the pressure applied.

One or more helical grooves may also be produced by gently pressing a sharp metal edge to the surface of a container while the container is rolled over a solid surface at a slight angle, either before or after the container is sealed to form a radioactive source. Spiral or helical grooves can be introduced using two tools which fit together allowing a gap the same diameter as the brachytherapy seed. Across the face of one tool is a diagonal raised profile which is the same shape and size as the desired groove. The titanium tube is rolled between the tools and the diagonal profile inscribes a helical or spiral groove across the tube as it rotates. The surface of the tools used must be roughened or coated to provide sufficient friction to the tube, enabling it to roll as the tools move.

The grooved surface of the present invention may also be achieved by etching, for example using a laser or water-jet cutter, or by electrolytic etching. Blasting, for example sand blasting, may also be used. Such blasting may be done dry, or wet as in water-jet blasting.

It is preferred that the grooves are introduced in such a way (e.g. compression or related techniques such as crimping), that material is not removed from the walls of the biocompatible container. This means that essentially the same amount of attenuation of radioactive dose by the low atomic number (Z) biocompatible container material (e.g. titanium) occurs. The result is that the radiation dose from the grooved seed is essentially the same as the dose from an ungrooved seed having the same radioisotope content. The retention of material can be achieved principally in two ways—by retaining a uniform wall thickness via deformation of both inner and outer container surfaces, or by compression so that the outer surface is grooved whereas the inner surface remains essentially planar. Preferably, the container wall thickness is uniform, i.e. the grooving process deforms or displaces the walls. The result is that the inner surface of the container is preferably also grooved—i.e. it is non-planar, and essentially a mirror image of the outer surface. Thus, it is preferred that both inner and outer surfaces of the container are grooved. A further advantage of grooves on the internal surface of the container is that the substrate carrying the radioisotope (e.g. $^{125}$I-iodide on silver wire), is less likely to move around within the container, potentially giving more consistent radiation dosimetry around the seed.

When the biocompatible container material is in the form of an ultrasound reflective inner material (e.g. metal), coated with a material which has comparable ultrasound transmission characteristics to water or mammalian tissue (e.g. organic polymers), then it is envisaged that the outer surface of such a device could be planar, and only the inner surface carry the echogenic grooves of the present invention.

When the biocompatible container material is metallic, e.g. titanium, it is also preferred that the metal is annealed prior to any mechanical working, compression etc of the metal. Annealing is known to those skilled in the art, and involves heating the metal to a high temperature below its melting point, followed by slow cooling back to ambient temperature either in vacuo or in an inert atmosphere, typically of argon. These precautions prevent any surface oxidation or other reaction between the hot metal and the surrounding atmosphere (e.g. nitride formation). For titanium, general annealing is carried out at 400–750° C., more preferably at 700±50° C. or at 25–55° C. below the beta transus temperature of 913±15° C. for recrystallisation annealing. Such annealed metals are more amenable to working, i.e. mechanical manipulation, reshaping etc., since they exhibit reduced risk of introducing weaknesses such as microfractures into the metal when the metal is subjected to stress.

Manufacture of radioactive seeds comprising a radioisotope inside a sealed metal or metal alloy container usually involves the provision of a suitable metal tube, one end of which is sealed (e.g. by welding) to form a canister. The radioisotope is then introduced into the canister and the remaining open end also sealed (e.g. by welding) to provide a sealed source or seed. Alternatively, a container or canister may be formed by stamping in a press from a core of metal or by casting, moulding or forming a core of molten metal, or by machining or drilling a solid core stock of metal, or by melting and reforming and solidifying metal stock or by fastening a cap to the end of a tube by means such as welding or threading, or by use of heat to expand and then contract the cap on cooling. The outer surface of the container may be grooved at any stage of the manufacturing process, including mechanical processing of the finished sealed radioactive source or seed to introduce grooves onto the surface.

For ease of manufacture, the grooving process preferably occurs before loading of the container with the radioisotope, more preferably on the non-radioactive metal tube before sealing of one end, and most preferably on a long section of metal tubing before it is cut into short segments suitable for use in forming canisters. The grooving process should not be such that the integrity of the container is compromised. In a further embodiment, the present invention provides precursors which comprise grooved biocompatible source container material, ready for assembly into sealed radioactive sources. Such precursors include e.g. tubing carrying the optimised grooves (dimensions and distribution) of the present invention, grooved tubing pre-cut into the necessary lengths or segments for seed or source manufacture, and such segments where one end is closed (e.g. by welding), to give a grooved canister ready for loading with the desired radioisotope.

In a still further aspect of the invention, there is provided a further method for the preparation of a radioactive source comprising a radioisotope and a sealed biocompatible container at least one part of the surface of which is grooved. The method comprises:
(i) grooving a surface or part of the outer surface of a non-radioactive precursor biocompatible container material;
(ii) loading a radioisotope into a suitably sized and sealed grooved biocompatible container precursor from step (i); and
(iii) sealing the biocompatible container.

For example, a suitable thin-walled metal tube such as a titanium metal tube may be mechanically deformed before insertion of the radioactive material and welding of the ends to form a sealed source. A smooth helical groove may be produced on the outer surface of the tube without affecting the thickness of the wall by use of a suitable crimping process. A support tool of cylindrical shape and with outer threads of a suitable pitch and depth may first be inserted into the metal tube. The support tool should fit tightly within the tube. A crimping tool may then be applied forcefully to the outer surface of the tube. The shape of the crimping tool should match that of the support tool. The crimping tool may consist of two or more parts, each part covering a different sector of the tube's surface. Following the crimping operation, the support tool may be removed by simply twisting due to its helical threaded shape.

The thickness of the biocompatible container wall may preferably be within the specifications set for conventional brachytherapy radioactive sources and seeds, or it may be selected as the optimum useful in brachytherapy by clinical experimentation. The wall thickness is dependent upon at least the energy of the radioisotope and the nature of the substrate. For titanium $^{125}$I seeds, the wall thickness is suitably in the range 35 to 65 μm. For example, conventional $^{125}$I seeds use 50 μm (0.05 mm) titanium cylinders for containment which are sufficient to block beta particles emitted by the $^{125}$I while letting enough gamma rays and low energy X-rays through for therapeutic impact. This is not inconsistent with the teaching that the depth of the surface grooves can be up to 60 μm, since the inner surface can be grooved as described above. If an aluminium container were used instead of titanium, the wall thickness would need to change in order to adequately capture any beta particles emitted. Correspondingly, if a polymeric container were used, it would need to be coated, for example with a titanium oxide "paint" or be plated with a metal to modify or block beta particle emissions if the plastic itself did not capture them. Higher energy sources may be used with thicker walled containers than lower energy sources.

The tube or container may optionally be provided with more than one type of groove. These may take the form of different depths, spacings, shapes or patterns, e.g. different parallel grooves (or corsets) or different advancing spiral or helical threads (which may be in the same or opposite sense of handedness), either alone or in combination.

The grooved treatment of an outer surface of the source of the invention may reduce the tendency of the sources to migrate or move once implanted inside a patient when compared to conventional smooth seeds. Grooves on two or more portions of the surface of a source are particularly suitable in this respect. Preferably, the grooving is sufficient to reduce the tendency of a source to migrate in vivo, but is not such that the sources cannot be delivered to the treatment site using conventional methodology and handling techniques. The smooth grooves and outer source surface which is substantially free from angularities of the present invention, are designed to minimise the potential for problems with the seeds 'sticking' in needles etc. Thus, it is highly desirable that the grooved seeds move smoothly within needles, cannulae etc. In fact the grooves may facilitate transmission by presenting a reduced surface area for frictional resistance to the inner contact surface of the needle or cannula. "Sticking" of seeds within loading devices is a known problem for clinicians and can present a safety risk. Thus, if undue pressure is applied to move a stuck seed, it is known that the seed capsule may rupture with consequent radioactive release, contamination etc.

Any conventional brachytherapy source may be grooved using the method of the invention. For example, the ultrasound visibility of the radioactive seeds disclosed in U.S. Pat. Nos. 5,404,309, 4,784,116 and 4,702,228 could be improved. These seeds comprise a capsule and two radioactive pellets separated by a radio-opaque marker within the capsule.

In a further aspect, the invention also provides a method of treatment of a condition in a mammal (for example, a human) which is responsive to radiation therapy, for example cancer, arthritis or restenosis, which comprises the temporary or permanent implantation of a radioactive source comprising a radioisotope within a sealed biocompatible container, wherein at least one part of the outer surface of the container is provided with the optimised grooves of the present invention, at the site to be treated within a patient for a sufficient period of time to deliver a therapeutically effective dose.

The invention will be further illustrated, by way of example, with reference to the following Figures:

The invention will be described with regard to the following description of the preferred embodiments thereof, and from the claims. The Examples and Figures are non-limiting.

Figure 2:
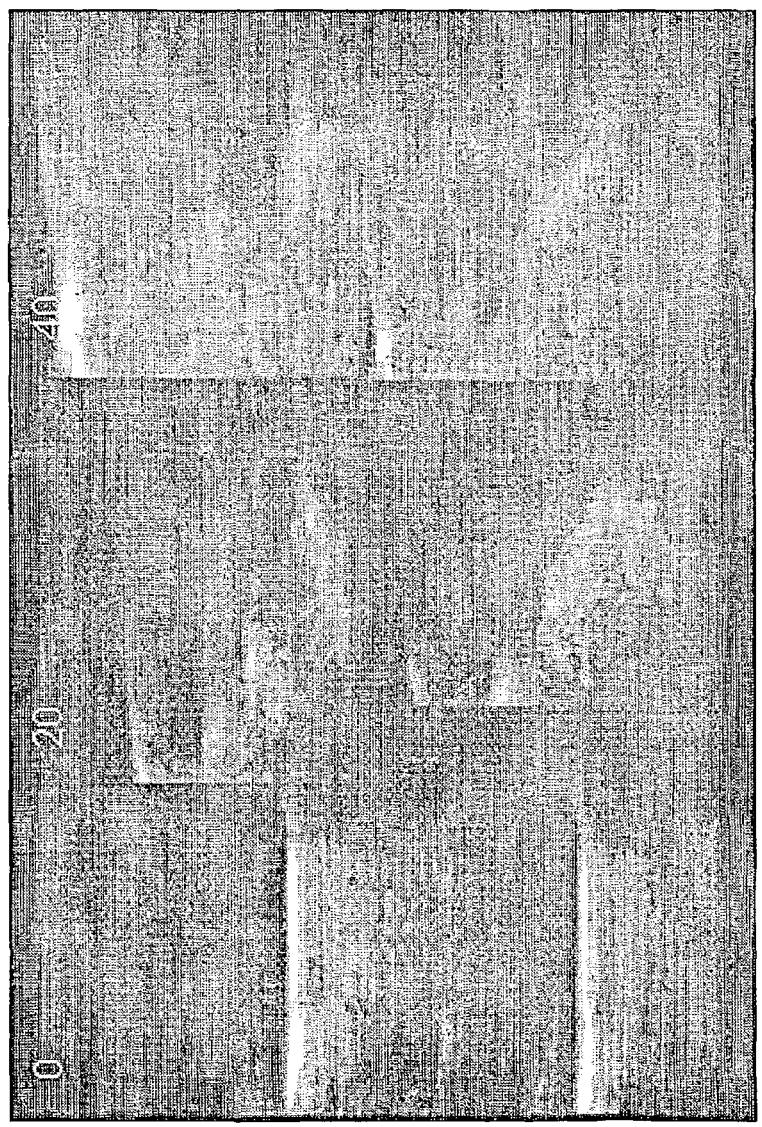
Figure 3:
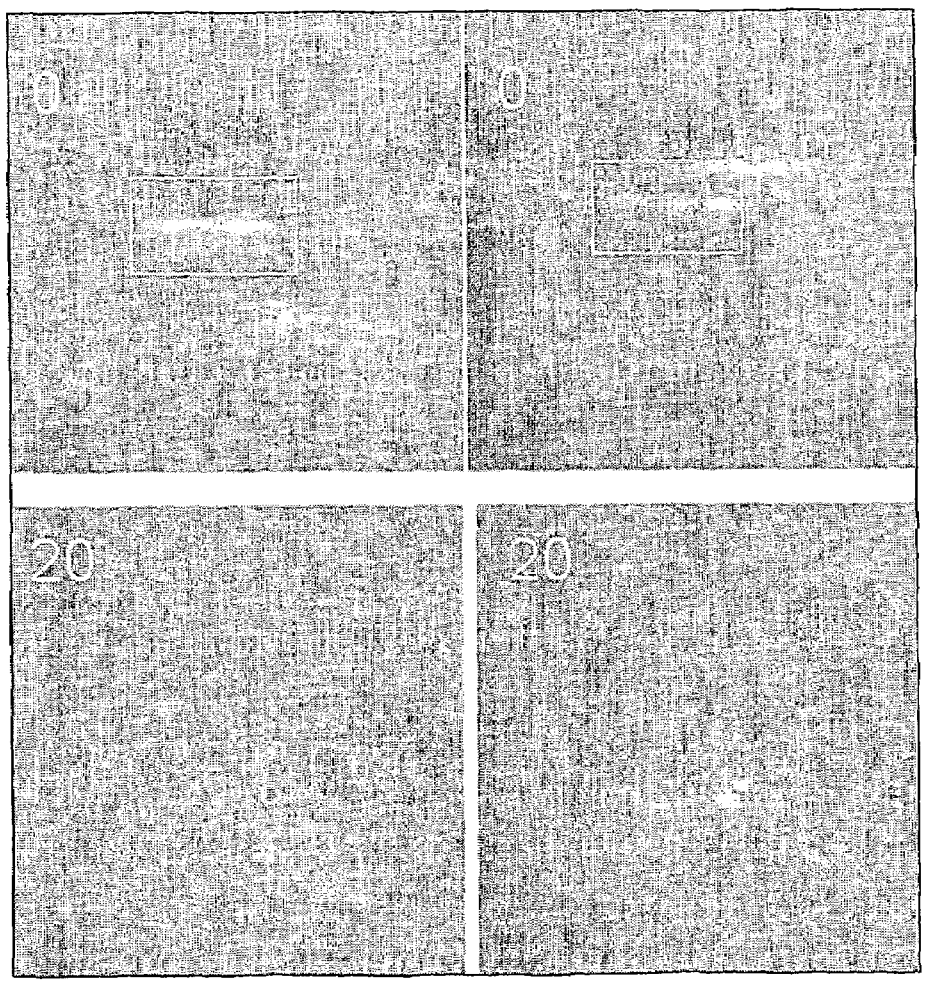
Figure 4:
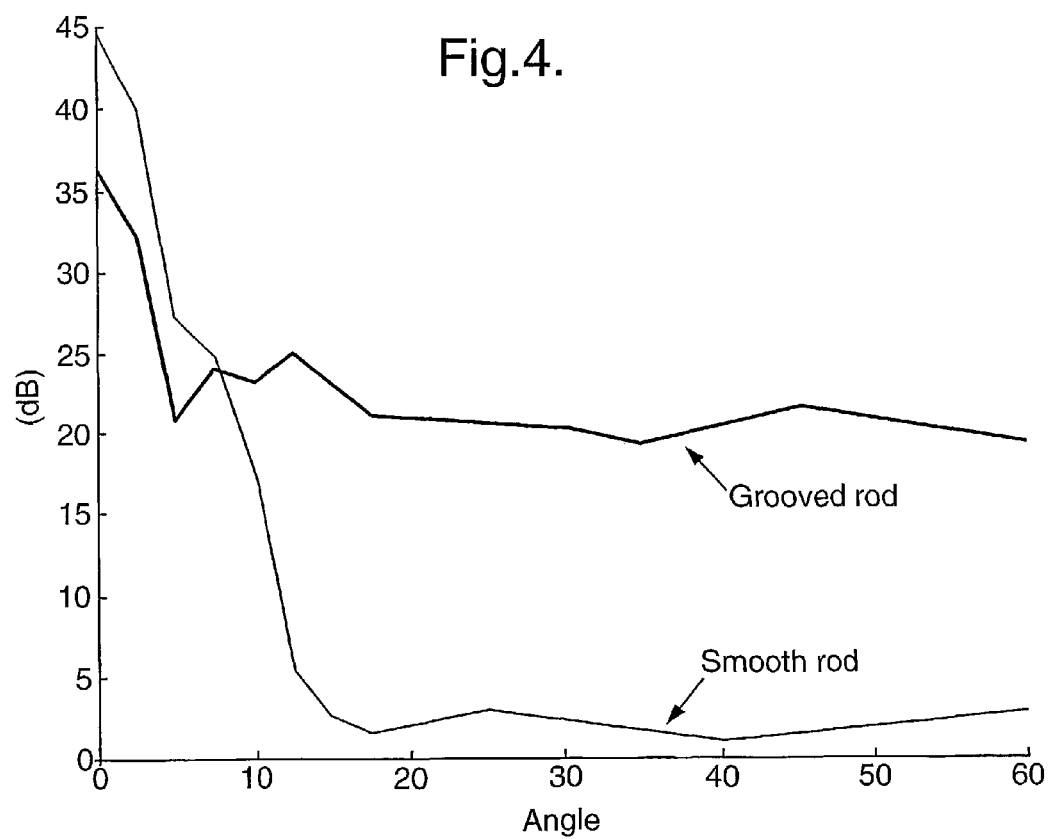
Figure 7A:
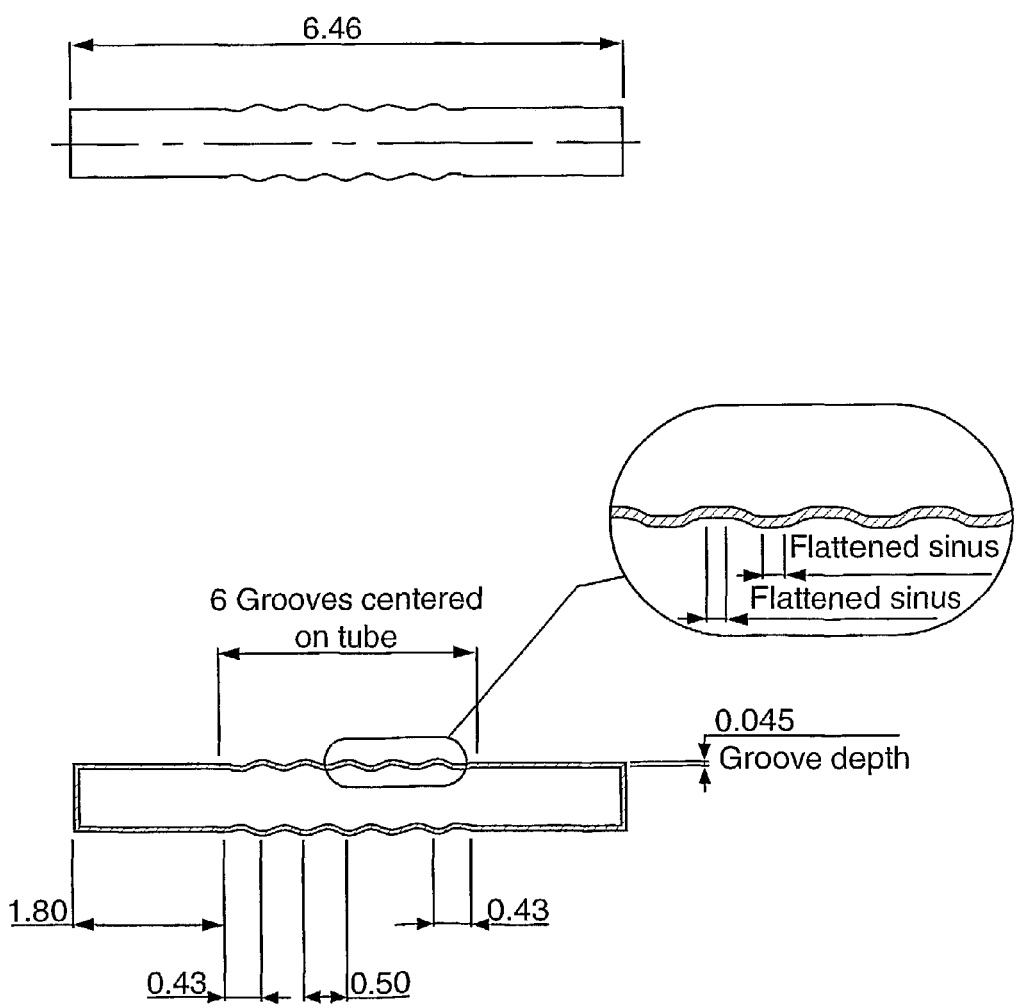

FIG. 2 compares ultrasound images from grooved and ungrooved steel rods at 0, 20 and 40 degrees from orthogonal;

FIG. 3 compares ultrasound images from grooved and ungrooved steel rods in excised dog prostate tissue;

FIG. 4 compares the reflected ultrasound signal intensity at various angles of reflection from grooved and ungrooved steel rods;

FIGS. 5 compares the ultrasound signal intensity from a grooved titanium canister (image shown) with a corresponding ungrooved titanium canister, at various angles;

FIG. 6 compares the ultrasound signal intensity from grooved steel rods with curved and angular groove profiles;

FIG. 7A shows an expanded view of a grooved tube used as a precursor for a preferred radioactive source container;

FIG. 7B shows an expanded view of a preferred radioactive source container;

FIG. 8 compares the reflected ultrasound signal intensity at various angles of reflection from a grooved and a smooth radioactive source container.

The invention will be further illustrated with reference to the following non-limiting Examples:

EXAMPLE 1

A wide band imaging ultrasound transducer ATL L10-5 was mounted in the wall of a water tank. The transducer was connected to an ATL HDI 5000 ultrasound scanner and imaging was performed at 6.5 MHz, a typical imaging frequency used in clinical transrectal ultrasound.

A brachytherapy seed was mounted on a holder located 50 mm from the transducer surface, which could be rotated to defined angles in relation to the direction of the ultrasound beam. The seed was glued on to the tip of a needle protruding from the specimen holder with cyanoacrylate glue so that the seed's centre of gravity coincided with the rotational axis of the holder. The angular rotation could be set with half a degree accuracy, which is of great importance given the high angular dependency of the ultrasound backscatter. The holder could also be adjusted by translation to position the seed in the focal point of the transducer and fixed throughout the experiments.

A series of measurements mapping the ultrasound backscatter of each of the seeds and test objects throughout the full range of incidence angles (−65 to +65 degrees) were performed. Digital images were stored for quantitative analysis of echo signal intensity with a custom-made image analysis system. An angular reflection index was defined as the range of angles where the echo signal is above a threshold defined to be 20 dB below the maximum signal intensity of a smooth surface test object at orthogonal incidence.

EXAMPLE 2

A smooth steel rod and a rod with a square surface pattern was imaged in vitro as described in Example 1. Images are acquired at 0, 20 and 40 degrees rotation, and are shown in FIG. 2. The upper series of images is a smooth 0.8 mm diameter, 6.5 mm length steel rod while the lower series is a similar steel rod with a cut surface with 0.1 mm wide helical square grooves, having a spacing of 0.54 mm and with a depth of 0.05 mm.

EXAMPLE 3

An excised dog prostate was imaged in a water tank with an ATL HDI 5000 scanner using an imaging frequency of 6.5 MHz. Two steel rods as described in Example 2 were implanted using an 18G needle. The prostate with the rods implanted was then rotated and imaged at different angles—see FIG. 3.

EXAMPLE 4

Two 0.8 mm diameter, 6.5 mm length solid steel rods, one with a smooth surface and one with helical square grooves as in Examples 2 and 3 (pitch 0.54 mm, width 0.1 mm and depth 0.05 mm) were imaged at different rotational angles as described in Example 1. The signal intensity from the centre of the rods were measured and plotted against angle—see FIG. 4.

EXAMPLE 5

Two 0.8 mm diameter, 6.5 mm length titanium canisters, one with a smooth surface, and one with a sinusoidal helical surface pattern, were imaged at different rotational angles as described in Example 1. The signal intensity from the centre of the canisters was measured and plotted against angle. The sinusoidal surface pattern had a groove amplitude of 0.04 mm and a spacing/pitch of 0.5 mm. The results are shown in FIG. 5.

EXAMPLE 6

Two 0.8 mm diameter, 6.5 mm length steel rods, one with a smooth surface and one with a circular square surface pattern (i.e. notches or grooves with sharp corners, i.e. square, that make circular parallel bands) were imaged at different rotational angles as described in Example 1. The signal intensity from the centre of the canisters were measured and plotted against angle. The circular square groove pattern had an amplitude of 0.070 mm, width of 0.2 mm and a spacing/pitch of 0.5 mm. The results are shown in FIG. 6.

EXAMPLE 7 (ANNEALING PROCEDURE)

A titanium pipe 500 mm long and of 20 mm diameter, fitted with an argon supply (99.99% purity, flow 5 dm$^3$/min) at one end was used. The pipe was flushed with argon for 30 min prior to loading. Non-radioactive, sealed titanium canisters of dimensions equivalent to seeds, were loaded into a porcelain ship, which was then introduced into the open end of the pipe. The pipe was inserted into a pre-heated electric furnace with thermocouple temperature control maintained at 700° C. The pipe was kept in the furnace for 30 min (15 min to heat to 700° C., and 15 min at 700° C.), then the oven was switched off and the pipe and dummy seeds allowed to cool to ambient whilst maintaining the argon atmosphere.

EXAMPLE 8

A titanium tube of nominal length 6.46 mm and nominal diameter 0.8 mm, with nominal 0.5 mm wall thickness was pressed in a die to produce 6 circular circumferential flattened sinusoidal grooves. The grooves had a nominal depth of 0.045 mm, nominal spacing of 0.50 mm, and nominal width of 0.25 mm. The grooved tube thus obtained is shown in FIG. 7A. The tube was annealed using a process analogous to that described in Example 7. One end of the grooved tube was sealed by welding and a silver wire, 2.75 mm in length and 0.51 mm in diameter was inserted into the titanium tube before sealing by welding the other end. The resulting dummy seed is shown in FIG. 7B. Ultrasound imaging of the dummy seeds was performed according to the method described in Example 1, using an equivalent non-grooved dummy seed as a comparison, results are shown in FIG. 8.

EXAMPLE 9

A titanium seed is prepared as described in Example 8 but is loaded with a silver wire carrying $^{125}$I with activities up to 50 mCi. The $^{125}$I silver wire is prepared essentially as described in U.S. Pat. No. 4,323,055.

Figure 1A:
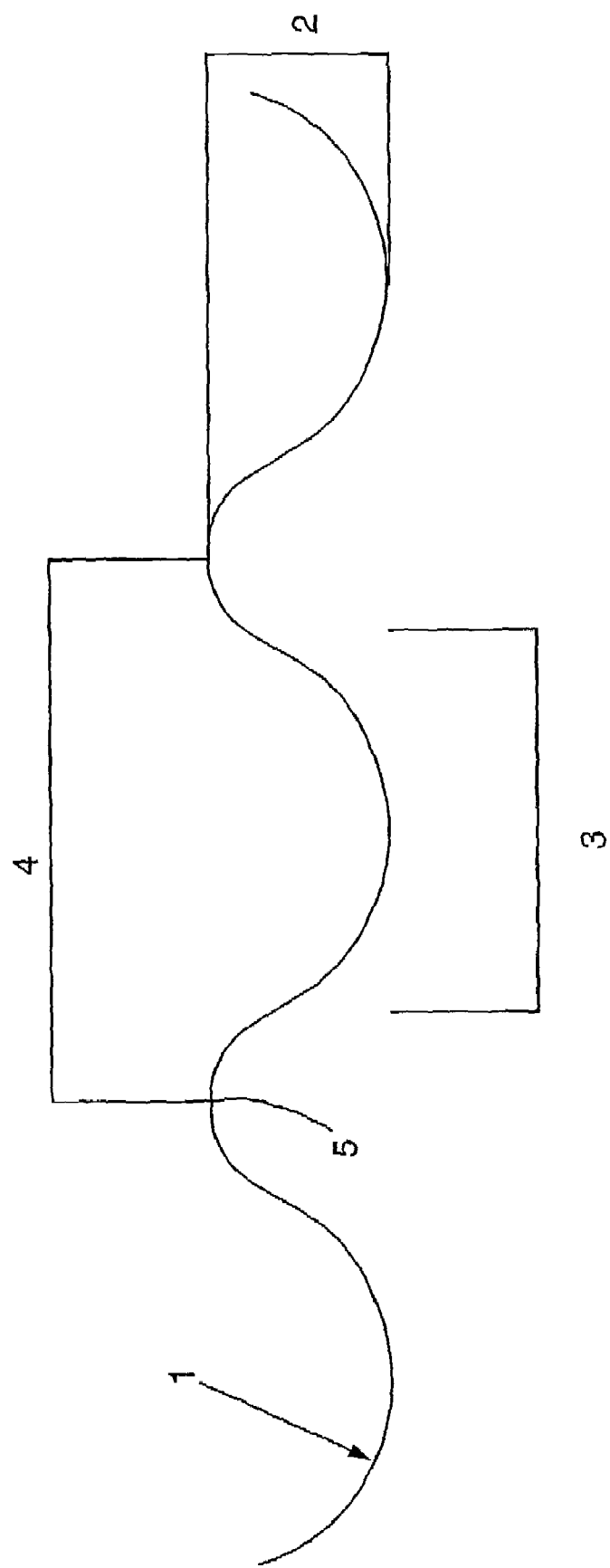
FIG. 1A illustrates the radioactive source surface according to the invention.

The figures will now be described in more detail:

FIG. 1A is a schematic illustration of part of a source surface (not to scale), with non-sinusoidal grooves [1]. The amplitude or depth [2] of the grooves is 20 to 60 micrometers. The width [3] of the grooves is 200 to 500 micrometers, and the groove spacing [4] is in the range 300 to 700 micrometers. The ridges [5] extend to the outer surface of the source, and may be convex (as shown), or substantially planar.

Figure 1B:
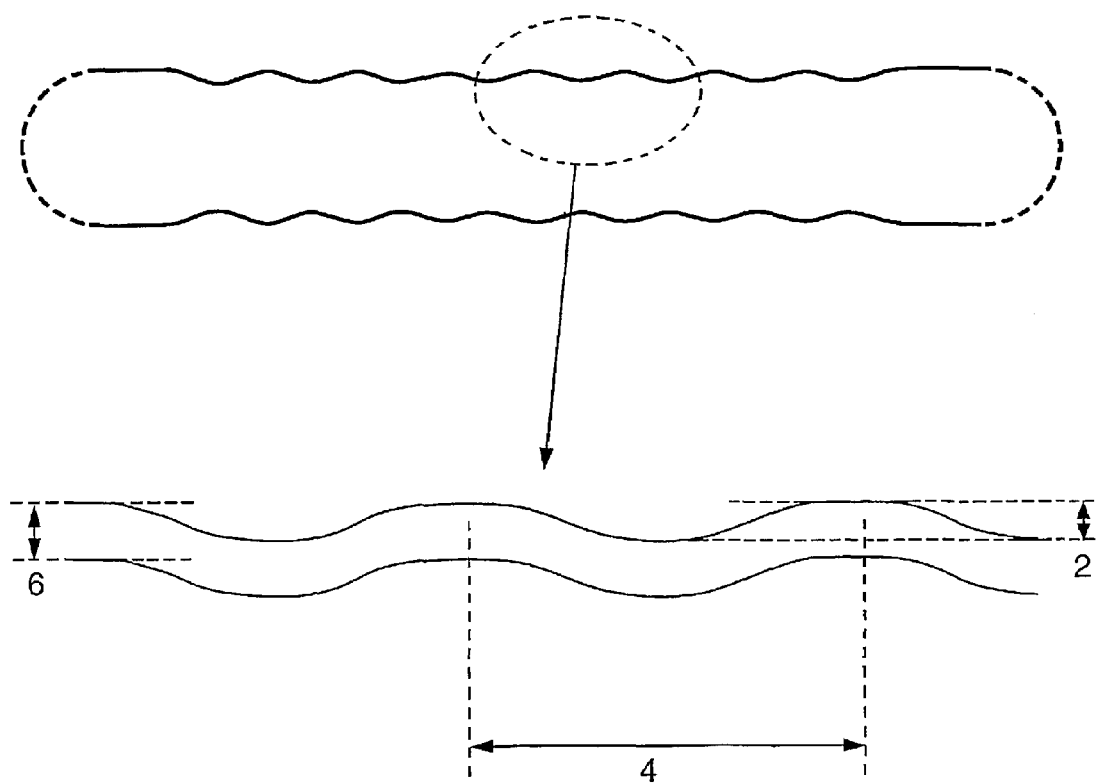
FIG. 1B shows an expanded view of a grooved radioactive source container wall material according to the invention.

FIG. 1B is an expanded view of a preferred grooved container wall design having a flattened sinusoidal profile, showing a grooved inner and outer wall surface. The spacing [4], depth [2] and uniform container wall thickness [6] are shown.

FIG. 2 shows that at 20 and 40 degrees of rotation of the rod relative to the incident ultrasound energy, only the ends of the smooth rods are visible, whilst the full length of the grooved rod is visible for 0, 20 and 40 degrees rotation. Note the visibly increasing angle of the corseted rod to the horizontal at 20 and 40 degrees.

FIG. 3 (left panels) shows an image of a blank (i.e. ungrooved or smooth) steel rod, and the right panel shows a steel rod with a grooved surface as in Example 2 (0.1 mm wide helical square grooves spaced at 0.54 mm and with a depth of 0.05 mm). The Example shows clearly that the cut rod is more visible than the blank rod at 20 degrees of rotation. At orthogonal ultrasound beam incidence (upper panels) both rods are easily identifiable, while at an angle (lower panels) only the grooved rod is readily identifiable.

FIG. 4 shows that the reflected signal intensity from the grooved rod (upper line) is weaker than that of the smooth rod (lower line) at small angles, but much stronger for angles above about 10 degrees.

FIG. 5 shows that the reflected signal intensity from the modified sinusoidal shaped grooved surface of a titanium canister (upper line), is somewhat weaker than that of the smooth canister (lower line) at small angles, but significantly stronger for angles above about 10 degrees.

FIG. 6 shows that the reflected signal intensity from a circular square grooved metal rod (upper line), is much weaker than that of a smooth rod at small angles, but stronger for large angles.

FIG. 7A shows a titanium tube having a preferred configuration of grooves, used in the manufacture of a preferred radioactive source container according to the invention.

FIG. 7B shows the radioactive source container obtained by loading a carrier into the tube shown in FIG. 7B and sealing both ends.

FIG. 8 shows that the reflected signal intensity from a grooved radioactive source container (solid line) is stronger than that of a smooth radioactive source container (dotted line) at large angles.

What is claimed is:

1. A radioactive source suitable for use in brachytherapy, which comprises a radioisotope within a sealed biocompatible container, wherein at least a portion of the outer surface of the container comprises a series of grooves which have:
   (i) a depth of 5 to 100 micrometers,
   (ii) a width of 200 to 500 micrometers,
   (iii) a spacing of 300 to 700 micrometers.

2. The radioactive source of claim 1, wherein the grooves are of curved cross-section.

3. The radioactive source of claim 1, wherein the grooved outer surface of the radioactive source is approximately sinusoidal or flattened sinusoidal in profile.

4. The radioactive source of claim 1, wherein the grooves are formed in such a way that the wall thickness of the biocompatible container material is maintained.

5. The radioactive source of claim 1, wherein the groove depth is 30 to 50 micrometers.

6. The radioactive source of claim 1, wherein the groove spacing is 450 to 550 micrometers.

7. The radioactive source of claim 1, wherein the groove width is 225 to 275 micrometers.

8. The radioactive source claim 1, wherein the outer surface of the container is provided with 4 to 7 circular circumferential grooves.

9. The radioactive source of claim 1, wherein the biocompatible container comprises annealed titanium.

10. A delivery system for brachytherapy, which comprises:
  (i) a substantially linear elongated member made from a material which is absorbable in living tissue,
  (ii) a plurality of discrete radioactive sources as claimed in claim 1 dispersed therein.

11. Biocompatible tubing suitable for use as a component of the radioactive sources of claim 1, having at least one open end characterised in that at least a portion of the outer surface of the tubing comprises a series of curved grooves which have:
  (i) a depth of 5 to 100 micrometers,
  (ii) a width of 200 to 500 micrometers,
  (iii) a spacing of 300 to 700 micrometers,
  wherein the grooved outer surface is approximately sinusoidal or flattened sinusoidal in profile.

12. The tubing of claim 11, where the tubing material comprises annealed titanium.

13. A method of treatment of a condition responsive to radiation therapy which comprises temporary or permanent implantation of a radioactive source according to claim 1.

* * * * *